United States Patent
Zenobi-Wong et al.

(10) Patent No.: US 9,937,257 B2
(45) Date of Patent: Apr. 10, 2018

(54) SULFATED ALGINATE HYDROGELS FOR CELL CULTURE AND THERAPY

(71) Applicant: ETH Zurich, Zurich (CH)

(72) Inventors: Marcy Zenobi-Wong, Zurich (CH); Gemma Palazzolo, Zurich (CH); Rami Mhanna, Zurich (CH); Jana Becher, Jena (DE); Stefanie Moller, Jena (DE); Matthias Schnabelrauch, Jena (DE)

(73) Assignee: ETH Zurich, Zurich (CH)

( * ) Notice: Subject to any disclaimer, the term of this patent is extended or adjusted under 35 U.S.C. 154(b) by 188 days.

(21) Appl. No.: 14/441,177

(22) PCT Filed: Nov. 4, 2013

(86) PCT No.: PCT/EP2013/003301
§ 371 (c)(1),
(2) Date: May 7, 2015

(87) PCT Pub. No.: WO2014/072035
PCT Pub. Date: May 15, 2014

(65) Prior Publication Data
US 2015/0290327 A1 Oct. 15, 2015

(30) Foreign Application Priority Data

Nov. 7, 2012 (EP) .................................. 12007560
Nov. 19, 2012 (EP) .................................. 12007934

(51) Int. Cl.
| | | |
|---|---|---|
| A61K 47/36 | (2006.01) | |
| A01N 1/02 | (2006.01) | |
| A61L 27/20 | (2006.01) | |
| A61L 27/38 | (2006.01) | |
| A61L 27/52 | (2006.01) | |
| C12N 5/00 | (2006.01) | |
| A61K 35/28 | (2015.01) | |
| A61K 35/30 | (2015.01) | |
| A61K 35/32 | (2015.01) | |
| A61K 35/33 | (2015.01) | |
| A61K 35/407 | (2015.01) | |
| A61K 35/545 | (2015.01) | |

(52) U.S. Cl.
CPC ............ *A61K 47/36* (2013.01); *A01N 1/0231* (2013.01); *A61K 35/28* (2013.01); *A61K 35/30* (2013.01); *A61K 35/32* (2013.01); *A61K 35/33* (2013.01); *A61K 35/407* (2013.01); *A61K 35/545* (2013.01); *A61L 27/20* (2013.01); *A61L 27/383* (2013.01); *A61L 27/3804* (2013.01); *A61L 27/52* (2013.01); *C12N 5/0012* (2013.01); *A61L 2430/06* (2013.01); *A61L 2430/32* (2013.01); *C12N 2533/74* (2013.01)

(58) Field of Classification Search
CPC ....................................................... A61K 47/36
See application file for complete search history.

(56) References Cited

U.S. PATENT DOCUMENTS

| | | | |
|---|---|---|---|
| 5,866,165 A | 2/1999 | Liu et al. | |
| 7,517,856 B2* | 4/2009 | Cohen | ............... A61K 47/4823 514/1.1 |
| 7,988,962 B2 | 8/2011 | Verbruggen et al. | |

FOREIGN PATENT DOCUMENTS

WO    WO 2008/067655    6/2008

OTHER PUBLICATIONS

Arlov, Hepain analogs created by sulfatin of alginates using a chemenzymatic strategy, Norwegian University of Science and Technology, May 2012.*
Re'em et al.: Biomaterials, vol. 33. Oct. 22, 2011 (Oct. 22, 2011), pp. 751-761.
Freeman et al.: Biomaterials, vol. 29, 2008, pp. 3260-3268.

* cited by examiner

*Primary Examiner* — Taeyoon Kim
*Assistant Examiner* — Tiffany M Gough
(74) *Attorney, Agent, or Firm* — JMB Davis Ben-David (57) ABSTRACT

The present invention relates to a method for providing an embedded mammalian cell, comprising the steps of providing an alginate sulfate in aqueous solution; reacting the alginate sulfate to form a hydrogel in a gelation step, providing a precursor cell, and embedding the precursor cell in the sulfated alginate hydrogel in an embedding step, thus yielding an sulfated alginate hydrogel embedded cell. The invention further relates to sulfated alginate hydrogels, and cellular grafts comprising a mammalian cell embedded in sulfated alginate hydrogel.

9 Claims, 5 Drawing Sheets

SULFATED ALGINATE HYDROGELS FOR CELL CULTURE AND THERAPY

CROSS-REFERENCE TO RELATED APPLICATIONS

This is the U.S. National Stage of International Application No. PCT/EP2013/003301, filed Nov. 4, 2013, which was published in English under PCT Article 21(2), and which in turn claims the benefit of European Patent Application Nos. 12007560.1 filed on Nov. 7, 2012 and 12007934.8 filed Nov. 19, 2012.

TECHNICAL FIELD

The present invention relates to sulfated alginate hydrogels and their use in tissue engineering and regenerative medicine.

BACKGROUND

The healing of cartilage lesions with currently available cell based therapies is hampered by the inconsistent retention and growth of the transplanted cells.

Likewise, nerve regeneration following injury is inhibited by multiple signals coming from the microenvironment of the glial scar, and biomaterials with a potent capacity to stimulate neurogenesis would have a high clinical importance.

Figure 1:
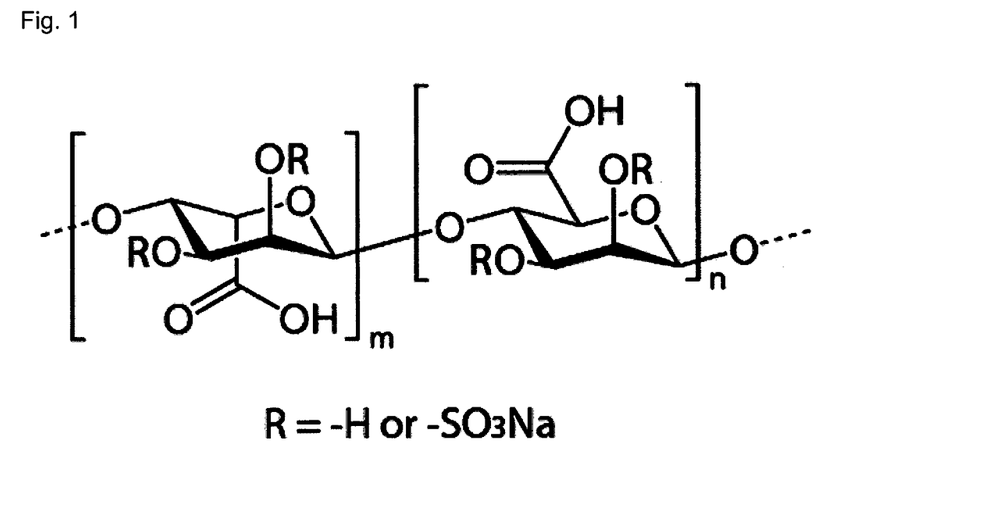

Alginates, as an example of such a biomaterial, are natural polymers that consist of two monosaccharides, β-D-mannuronic acid (M) and α-L-guluronic acid (G), arranged in homopolymeric (poly-mannuronate or poly-guluronate) or heteropolymeric block structures (FIG. 1). They can be extracted from brown seaweed and do not exert any strong immunological reaction when injected into mammalian tissues [Suzuki et al., Journal of Biomedical Materials Research. 1998; 39:317-22].

Alginate is fully biocompatible, FDA-approved and used widely in tissue engineering, regenerative medicine, cell encapsulation and drug delivery. Its properties can be tuned by varying the amount of α-L-guluronic acid (G) and (1,4)-linked β-D-mannuronic acid (M) and by functionalization with growth factors and adhesion molecules, such as a RGD-peptide (arginylglycylaspartic acid).

Alginate has been widely used, in combination with other biomaterials and/or functionalized with growth factors, as a drug delivery system and scaffold for tissue engineering. Francis et al. show that fibroblasts expressing brain-derived neurotrophic factor (Fb/BDNF) can be incorporated in alginate and guide neurite outgrowth of dorsal root ganglia (DRGs) [Francis et al., Journal of microencapsulation. 2011; 28:353-62]. Growth factors (GFs) can also bind directly to alginate, with their release being regulated by the disruption of ionic bridges between the positively charged factors and the poly-anionic alginate. NGF-grafted alginate/poly(gamma-glutamic acid) hydrogels have been used for inducing the neural differentiation of induced pluripotent stem cells [Kuo and Chang, Colloids and surfaces B, Biointerfaces. 2012; 102C:405-11]. Moreover, the sulfation of uronic acids of alginate provides specific and strong binding to heparin-binding proteins, some of which do not normally bind to pure alginate. For instance, an alginate sulfate scaffold can sustain basic fibroblast growth factor (bFGF) release to the extracellular medium [Freeman et al., Biomaterials. 2008; 29:3260-8], as well as TGF-β release, the latter inducing chondrogenic differentiation of human mesenchymal stem cells [Re'em et al, Biomaterials. 2012; 33:751-61].

Alginate sulfate has been shown to possess anticoagulant properties similar to that of heparin [Ronghua et al., Carbohydrate Polymers. 2003; 52:19-24].

It is the objective of the present invention to provide means and methods for tissue engineering and for regenerative treatment, particularly for the treatments of cartilage lesions or nerve damage.

The objective is attained by the subject-matter of the independent claims.

SUMMARY OF THE INVENTION

Definitions

The term "alginate sulfate", synonymously used as "sulfated alginate" in the context of the present specification, refers to a polysaccharide consisting of β-D-mannuronic acid (M) and α-L-guluronic acid (G) organized in homo- or heteropolymeric block structures (FIG. 1). Each monosaccharide unit contains 2 hydroxyl (—OH) groups available for sulfation. The alginate polymer can have a degree of substitution of sulfation (DSs) ranging from 0 to 2 per monomer (monosaccharide unit, either β-D-mannuronic acid or α-L-guluronic acid) or 0 to 4 per disaccharide unit (either β-D-mannuronic acid-α-L-guluronic acid, β-D-mannuronic acid-β-D-mannuronic acid or α-L-guluronic acid-α-L-guluronic acid), meaning between none and all of the available —OH groups are sulfated. The degree of sulfation dictates the physical and biological properties of the hydrogel that is composed of such a sulfated alginate polymer.

The term "hydrogel" in the context of the present specification refers to an aqueous polymer gel composition comprising 0.1 to 5% (m/m) of polymer. The term "sulfated alginate hydrogel", also referred to as "alginate sulfate hydrogel" in the context of the present specification, relates to a hydrogel according to the preceding definition, wherein the polymer is sulfated alginate.

According to one aspect of the invention, a method for providing an embedded mammalian cell is provided, wherein the method comprises the steps of
  providing a sulfated alginate in aqueous solution;
  reacting the sulfated alginate to form a hydrogel in a gelation step,
  providing a precursor cell, wherein particularly the precursor cell is derived from a mammal,
  embedding the precursor cell in the sulfated alginate hydrogel in an embedding step, thus yielding a sulfated alginate hydrogel embedded cell.

According to another aspect of the invention, a sulfated alginate hydrogel is provided, comprising a sulfated alginate with a degree of sulfation between 0.1 and 1 per monomer, particularly between 0.5 and 0.9 per monomer.

In some embodiments of any method or composition of matter (sulfated alginate hydrogel) aspect of the invention, the sulfated alginate hydrogel has a content of sulfated alginate of 0.1 to 5% (per mass: m/m or wt %).

In some embodiments of any of the above aspects of the invention, the sulfated alginate is characterized by a β-D-mannuronic acid:α-L-guluronic acid molar fraction of 20:80 (β-D-mannuronic acid:α-L-guluronic acid), 30:70 (β-D-mannuronic acid:α-L-guluronic acid), 40:60 (β-D-mannuronic acid:α-L-guluronic acid), 50:50 (β-D-mannuronic acid:α-L-guluronic acid) or 60:40 (β-D-mannuronic acid:α-L-guluronic acid). In some embodiments, the sulfated alginate is characterized by a β-D-mannuronic acid:α-L-guluronic acid molar fraction of 40:60 (β-D-mannuronic acid: α-L-guluronic acid).

In some embodiments of any of the above aspects of the invention, the sulfated alginate has a degree of sulfation between 0.1 and 1 per monomer, particularly between 0.5 and 0.9 per monomer. In some embodiments, the sulfated alginate has a degree of sulfation between 0.2 and 2 per disaccharide unit, particularly between 1 and 1.8 per disaccharide unit.

An advantage of the sulfated alginate hydrogel of the invention is that it facilitates gel formation of sulfated alginate in the presence of Ca2+ ions, which was previously not possible. The presence of sulfate groups increases the negative charge of the sulfated alginate polymer chain, causing repulsion of the chains and interference with the $Ca^{2+}$/carboxyl interaction, thereby inhibiting gel formation at higher degrees of sulfation. The higher the degree of substitution or sulfation, the softer, and more porous the sulfated alginate hydrogel becomes. Furthermore, the presence of sulfate groups in the sulfated alginate is particularly advantageous for differentiation and growth of the embedded precursor cell. The molecular interactions between two sulfate alginate chains are weaker and the overall pore size of the material increases with sulfation. This provides a softer material that the cells are able to deform and rearrange, using their own contractility mechanisms.

In some embodiments of any of the above aspects of the invention, the sulfated alginate comprises or is essentially constituted of sulfated alginate that is further modified by aldehyde moieties, carboxyl moieties, amino moieties, vinyl sulfone moieties, thiol moieties, saturated or unsaturated ester or ether groups, wherein particularly non-sulfated hydroxyl groups or carboxyl groups of the sulfated alginate are modified by the above mentioned moieties or groups. One advantage of the modification of hydroxyl or carboxyl groups of the sulfated alginate is that these modifications can be used to crosslink the gels using Michael addition (vinyl sulfone, thiol), in which case calcium gelation is not required for hydrogel formation.

In some embodiments of any of the above aspects of the invention, the sulfated alginate comprises or is essentially constituted of sulfated alginate, wherein not more than 50% of hydroxyl groups are modified by aldehyde moieties, carboxyl moieties, amino moieties, vinyl sulfone, thiol moieties, saturated or unsaturated ester or ether groups, and wherein particularly the sulfated alginate has a degree of sulfation between 0.1 and 1 per monomer, particularly between 0.5 and 0.9 per monomer.

In some embodiments of any of the above aspects of the invention, the sulfated alginate comprises or is essentially constituted of sulfated alginate that is further modified by covalent attachment of acrylate or methacrylate ester groups to non-sulfated hydroxyl groups of sulfated alginate. In some embodiments, the degree of acrylation or methacrylation is between 0.1 and 0.5 per monomer, meaning that between 10% and 50% of the hydroxyl groups per monomer are modified by covalent attachment of acrylate or methacrylate, particularly 0.3 per monomer, meaning that 30% of the hydroxyl groups per monomer are modified by covalent attachment of acrylate or methacrylate, wherein particularly the sulfated alginate has a degree of sulfation between 0.1 and 1 per monomer, particularly between 0.5 and 0.9 per monomer.

In some embodiments of any of the above aspects of the invention, the sulfated alginate is provided in mixture with other hydrogel forming polymers and scaffolds. One advantage of the addition of a second polymer is an increase in mechanical stability of the sulfated alginate hydrogel. Particularly, an electrospun or porogen-leached stiff porous scaffold may be backfilled with sulfated alginate. Non-limiting examples for such a second polymer include poly (ε-caprolactone), PLGA (poly(lactic-co-glycolic) acid and PMMA (poly[methyl methacrylate]). Another advantage of the addition of a second polymer is the possibility to add functional groups, which allow adhesion to, for example, a cartilage lesion. Particularly, oxidized alginate may be added to the mix, to allow adhesion to the free amine groups of the collagen of the cartilage surface. The term "oxidized alginate" in the context of the present specification particularly refers to an alginate, wherein one or more carbon atoms of the alginate bearing a hydroxyl group are oxidized to the ketone form, wherein particularly such ketone carbon atom is reactable with an amine group to form a Schiff-base. Likewise, the term "oxidized sulfated alginate" refers to a sulfated alginate, wherein one or more carbon atoms of the sulfated alginate bearing a non-sulfated hydroxyl group are oxidized to the ketone form, wherein particularly such ketone carbon atom is reactable with an amine group to form a Schiff-base.

In some embodiments of any of the above aspects of the invention, the sulfated alginate is mixed with a second polymer that can be crosslinked, particularly by Schiff base covalent binding, Michael addition reaction or radical polymerization. A non-limiting example is mixing sulfated alginate with chondroitin sulfate or hyaluronic acid that is methacrylated and can form an interpenetrating hydrogel with UV light and a photoinitiator. Further non-limiting examples for such second polymers include methacrylated chondroitin sulfate, methacrylated hyaluronic acid, and PEG (polyethylene glycol)-diacrylate.

In some embodiments of any of the above aspects of the invention, the sulfated alginate hydrogel is formed in the gelation step by
  a. ionic crosslinking using calcium ions, particularly in the form of calcium chloride, calcium carbonate or calcium sulfate or other two- or three-valent cations,
  b. Schiff base covalent binding between an oxidized sulfated alginate or an oxidized sulfated alginate comprised with the sulfated alginate and an amine- or thiol-bearing polymer such as chitosan,
  c. Michael addition reaction,
  d. radical polymerization of alginate sulfate bearing additional polymerizable groups such as methacrylate or acryl.

The term "ionic crosslinking" in the context of the present specification particularly refers to electrostatic interaction between the $Ca^{2+}$ and carboxyl groups of the two alginate polymer chains.

In some embodiments of any of the above aspects of the invention, the electrostatic interactions occur between guluronic acid residues of two alginate polymer chains.

In some embodiments, forming of the sulfated alginate hydrogel is initiated by contacting sulfated alginate in aqueous solution with $Ca^{2+}$ ions, particularly with $CaCl_2$, wherein particularly the gelation starts at the surface of the polymerizing hydrogel and proceeds towards the center of the polymerizing hydrogel as the $Ca^{2+}$ ions diffuse into the gel.

In some embodiments, forming of the sulfated alginate hydrogel is performed with $CaCO_3$ and D-glucono-d-lactone and/or $CaSO_4$ and D-glucono-d-lactone added to the aqueous solution in which the sulfated alginate is provided, wherein particularly calcium ions are slowly released from $CaCO_3$ or $CaSO_4$ that are not soluble in water at neutral pH, and wherein particularly D-glucono-d-lactone is hydrolyzed and acidifies the solution thereby increasing the release of calcium ions. One advantage of these embodiments is that a more homogeneous hydrogel forms as a result of the process herein described.

In some embodiments, acrylic, vinyl sulfone maleimide or acrylate groups previously reacted with the hydroxyl groups of sulfated alginate represent the Michael acceptors while the Michael donor is a thiolate anion or a thiol group present on another polymer such as for example a polyethylene glycol polymer bearing the thiol group.

In some embodiments, the polymerizable group is a methacrylate group or an acryl group. In some embodiments, the methacrylate or acrylate group reacts with the hydroxyl groups of sulfated alginate. In some embodiments, the polymerizable group is used to generate radicals when exposed to UV or neon light in the presence of a photo-initiator such as lithium acylphosphinate LAP or eosin Y, thus producing a radical chain reaction.

In some embodiments, the sulfated alginate hydrogel comprises or is essentially constituted of sulfated alginate having a degree of sulfation from 0.1 to 1.8 per monomer, particularly 0.1 to 1 per monomer, more particular 0.5 to 0.9 per monomer. In some embodiments, the sulfated hydrogel comprises or is essentially constituted of sulfated alginate having a degree of sulfation between 0.2 and 2 per disaccharide unit, particularly between 1 and 1.8 per disaccharide unit.

In some embodiments, the sulfated alginate hydrogel is characterized by a viscosity of 200 Pa/S. Such sulfated alginate hydrogel is preferably suitable for bioprinting, whereby it is possible to create complex 2D/3D structures made of multiple materials, cell types and molecules.

In some embodiments, the precursor cell is a central primary neuron, a peripheral primary neuron, a glial cell, a primary chondrocyte, a fibroblast, an osteoblast, a hepatocyte, an adult stem cell, an induced pluripotent cell, or a cell culture line cell.

In some embodiments, the precursor cell is a chondroprogenitor cell. In some embodiments, the chrondroprogenitor cell is a member of a chondroprogenitor cell line, wherein particularly the chondroprogenitor cell line is derived from a fetus.

In some embodiments, the sulfated alginate is formed by the reaction of alginate with chlorosulfonic acid or sulfurtrioxide, wherein particularly hydroxyl groups of the alginate polymer chain are substituted by sulfate groups.

According to another aspect of the invention, a sulfated alginate hydrogel is provided, comprising a sulfated alginate with a degree of sulfation between 0.1 and 1 per monomer, particularly between 0.5 and 0.9 per monomer.

In some embodiments, the sulfated alginate hydrogel has a content of sulfated alginate of 0.1 to 5% (m/m).

According to a further aspect of the invention, a method for culturing a mammalian cell is provided, wherein the method comprises a method for providing an embedded mammalian cell according to the invention and additionally, and subsequently, the steps of
maintaining the precursor cell under conditions of cell culture in a cell culture step, yielding a product cell,
isolating the product cell.

In some embodiments, the gelation step proceeds prior to the embedding step, the precursor cell is thus seeded onto the hydrogel, and subsequent to the cell culture step, and the product cell is isolated by depolymerizing or degrading the sulfated alginate hydrogel. In some embodiments, the precursor cell is embedded in the sulfated alginate prior to gelation and grows under in vivo conditions in the sulfated alginate hydrogel. In some embodiments, the precursor cell is embedded in the sulfated alginate prior to gelation and is then released from the sulfated alginate gel, particularly for implantation purposes, wherein particularly the sulfated alginate undergoes gelation, and after implantation the sulfated alginate hydrogel become infiltrated by migratory cells of the host, for example resident mesenchymal stem cells, or chondrocytes for cartilage and neural progenitor cells for nerve tissue.

In some embodiments, depolymerizing is performed by removal of the $Ca^{2+}$ ion, particularly by rinsing or contacting the sulfated alginate hydrogel with a $Ca^{2+}$ binding agent such citrate, EDTA, EGTA or a cationic resin, or by contacting the sulfated hydrogel with a dissolving sodium citrate buffer, comprising optionally EDTA.

According to yet another aspect of the invention, a cellular graft comprising a mammalian cell embedded in sulfated alginate hydrogel is provided.

In some embodiments, the cellular graft is obtained or obtainable by a method according to the invention or comprising a sulfated alginate hydrogel according to the invention.

In some embodiments, the mammalian cell is a central primary neuron, a peripheral primary neuron, or a glial cell.

In some embodiments, the mammalian cell is a primary chondrocyte or a mesenchymal stem cell.

In some embodiments, the mammalian cell is a fibroblast, an osteoblast, a hepatocyte, an adult stem cell or an induced pluripotent cell.

According to another aspect of the invention, the use of a cellular graft according to the invention for treating neural injury or degeneration is provided.

In some embodiments, the cellular graft of the invention is inserted or injected into a site of neural injury or degeneration following CNS or PNS injury.

In some embodiments, the use of a cellular graft of the invention for treating a cartilage lesion by transplantation of the cellular graft is provided, as an augmentation of the autologous chondrocyte implantation (ACI) procedure.

In some embodiments, the sulfated alginate hydrogel is cross-linkable to cartilage tissue via Schiff-based covalent binding of an oxidized alginate or an oxidized sulfated alginate comprised within the sulfated alginate hydrogel.

The following figures and examples further illustrate the invention and preferred embodiments thereof. The figures and examples are not to be construed to delimit the invention.

Wherever alternatives for single separable features are laid out herein as "embodiments", it is to be understood that such alternatives may be combined freely to form discrete embodiments of the invention disclosed herein.

BRIEF DESCRIPTION OF THE DRAWINGS

FIG. 1 Alginate sulfate chemical structure. The Degree of Sulfation (DS) per monomer ranges from $0 < DS \leq 2$ FIG. 2 Confocal image of E17 rat primary cortical neurons cultured in 2% alginate sulfate (DSs=1) for 7 days. Neurites start to elongate shortly after encapsulation and a dense network can be observed at day 7 in culture. Live imaging was obtained by staining neurons for 3 days following encapsulation with a cell tracker: the far-red fluorescent, lipophilic carbocyanine DiD (Life Technologies);

DETAILED DESCRIPTION OF CERTAIN EMBODIMENTS

Here, an invention is described, in which the addition of a sulfate group onto the polysaccharide alginate can potently alter the phenotype of primary cells that are encapsulated within the material. In particular, primary chondrocytes encapsulated within the sulfated hydrogel exhibit a more spread morphology, and proliferation is increased by 4-fold compared to cells within unmodified alginate that maintain a round morphology and divide very slowly. Furthermore, alginate sulfate prevents de-differentiation of primary chondrocytes as opposed to 2D culturing. Also primary neurons and induced pluripotent cells (iPSCs) seeded within sulfated alginate undergo extensive neurite formation. The sulfation of alginate is an inexpensive, abundant, easily handled and easily processed material, which can potently control the fate of both primary and stem cells within a 3D environment. The alginate sulfate is also suitable for being mixed with other polymers and generating composites.

The present invention provides the use of an alginate sulfate-based biomaterial for controlling the differentiation and proliferation of primary and stem cells used in regenerative medicine.

This material offers the advantages of being:
derivable from a natural, highly abundant and economically available source, highly biocompatible and with reversible gelation suitable for encapsulating a range of cells including but not limited to neurons, chondrocytes, hepatocytes, fibroblasts, induced pluripotent cells, adult and embryonic stem cells;
easily handled and processed;
tunable in terms of mechanical properties, particularly the stiffness, ranging from 0.5-6 kPa, particularly from 2-6 kPa (brain extracellular matrix) up to 100 KPa (cartilage), wherein particularly tuning may be achieved by varying the degree of sulfation, method of crosslinking with calcium, ratio of gluronic/manuronic composition or the structure by addition of further biopolymers such as a stiff porous scaffold composed of a polymer such as PLGA, PCL, PMMA for backfilling, or biopolymer such as methacrylated chondroitin sulfate, methacrylated hyaluronic acid and PEG-diacrylate, which particularly can be used for crosslinking of the sulfated hydrogel;
a potent promoter of neuronal outgrowth for regeneration of cells of the central and peripheral nervous system;
a potent promoter of connective tissue cell proliferation within a 3D environment, wherein particularly the sulfate groups introduced in the alginate polymer interferes with the calcium crosslinking to yield a structure that is both softer and has a more open pore structure, particularly the ionic crosslinking yields a material, which is more pliable and deformable for the cells than covalently crosslinked gels, and particularly the introduced sulphate groups provide biological motifs, with which the cells directly can interact, something they cannot do with unmodified alginate;
suitable for bioprinting, for example as described in US20120116568A1, and other rapid prototyping methods to create complex patterns of sulfation with multiple materials, cells and molecules;
combinable with other biopolymers to produce three dimensional (3D) structures where neural cells are guided along defined paths of high sulfation and repelled by regions of low sulfation;
obtainable with different degrees of sulfation that have dose-dependent effects on differentiation and proliferation (see FIG. 6);
a biomaterial that provides specific ligand binding motifs with which cell surface receptors (for example receptor protein tyrosine phosphatases) can interact;
able to provide gelation by multiple methods including but not limited to 1) ionic crosslinking using divalent cations, e.g. $Ca^{2+}$, $Ba^{2+}$, $Sr^{2+}$ in form of a salt solution or carbonate, 2) Schiff-base linkage (e.g. oxidized sulfate alginate linked with an amino bearing polymer like chitosan), 3) s-linked with electron acceptor (e.g. amines, thiols), through a Michael addition reaction and 4) free radical polymerization of sulfated methacrylated alginate in the presence of light and a photoinitiator.

Without wishing to be bound by theory, the inventors speculate that alginate sulfate has properties which mimic heparan sulfate. Heparan sulfate proteoglycans (HSPGs) positively influence neuronal growth and differentiation through several mechanisms. One involves the binding of HSPGs present in the extracellular matrix to type II receptor protein tyrosine phosphatases (RPTPs) that localize at the axonal growth cone and regulate neuronal growth and guidance [Coles et al., Science. 2011; 332:484-8]. Recently, heparan sulfate (HS) analogs have been described as good candidates for tissue repair. HS analogs are structurally and functionally similar to HS, but show the advantage of being resistant to enzymatic degradation. For example, peptide amphiphilic (PA) nanofibers have been efficiently used for inducing neurite outgrowth in combination with laminin [Mammadov et al., Acta biomaterialia. 2012; 8:2077-86]. The sulfation of heparan sulfate has proved to be crucial for establishing the neural lineage during early development. In fact, under-sulfation of heparan restricts the differentiative potential of mouse embryonic stem cells, preventing the formation of adipose and neural tissues [Forsberg et al., J. Biol. Chem. 2012; 287:10853-62]. HSPGs are also key regulators of angiogenic growth factors, thus controlling vascular development [Ferreras et al., Journal of Biological Chemistry. 2012; 287:36132-46] which can enhance nerve regeneration. Because of the high affinity of sulfated alginate to heparin-binding proteins, it can be considered an analog of HSPG, with great potential in neural growth and guidance. A recent patent on degradable nerve guides for nerve repair summarizes the properties of a large number of polymers including heparin, heparan sulfate, dextran sulfate and alginate on hydrogel formation. Nanofibers are coated with several extracellular matrix molecules including laminin and heparin, and one or more neurotrophic factors are grafted within the hydrogel [Hoke A, Lim S H, Liu X, Mao H Q. Hydrogel-grafted degradable nerve guides. USA: The Johns Hopkins University, Baltimore; 2011]. Because heparan sulfate is also found also in other tissues, such as liver, alginate sulfate can be considered useful for a broad range of applications in tissue regeneration. Furthermore, the inventors speculate that (also in the examples below) the action of alginate sulfate may be due to its analogy to the sulfated glycosaminoglycans present in the body tissues.

When unmodified alginate sponges were implanted in an in vivo spinal cord transection model in rats, outgrowth of axons from the injured spinal cord into the hydrogel was observed [Kataoka et al., Tissue engineering. 2004; 10:493-504]. Although this experimental evidence suggests alginate can stimulate axonal extension, sulfated alginate is much more potent. In terms of cartilage repair, chondrocytes proliferate very slowly in unmodified alginate. In sulfated alginate the proliferation of the cells is strongly induced.

Figure 2:
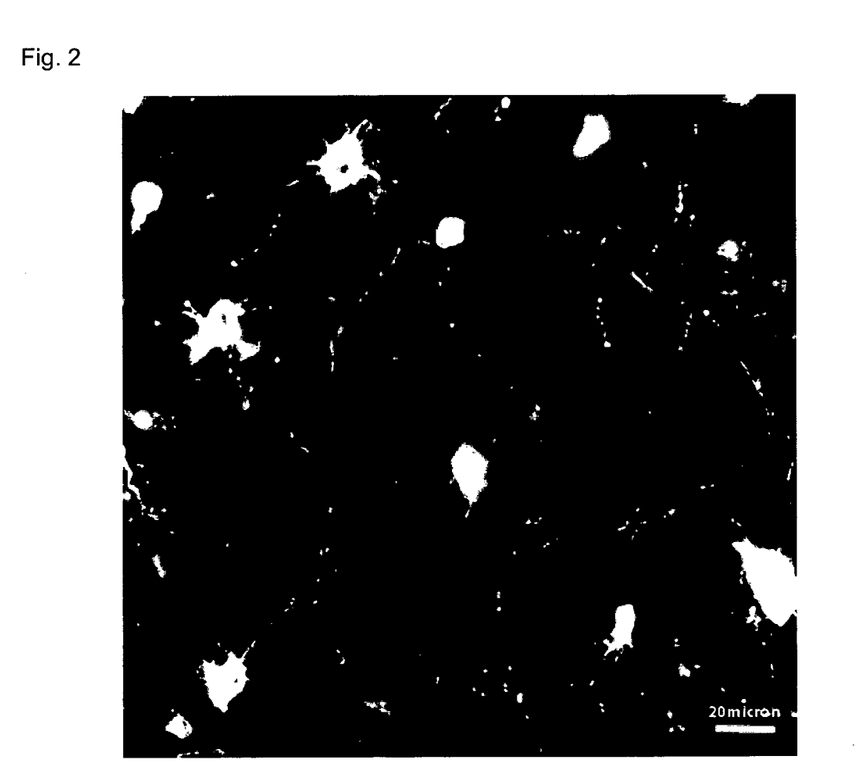
Figure 3:
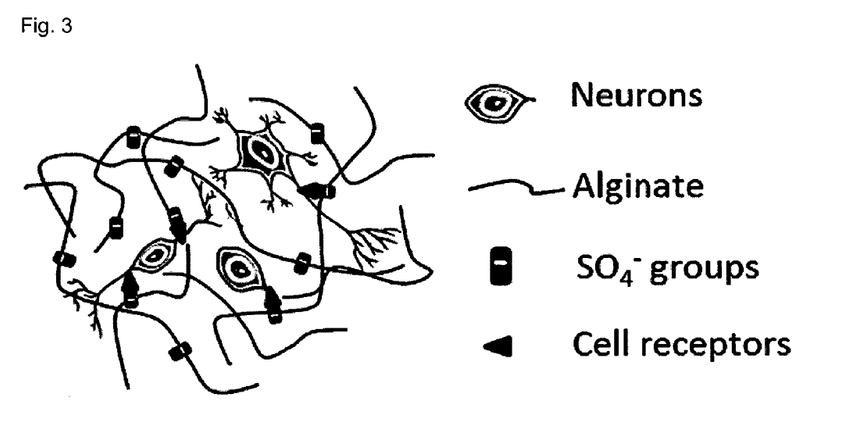
FIG. 3 Scheme of possible electrostatic interactions between the sulfate groups in alginate sulfate and membrane receptors present on neural cells, which turn into an induction of neurite elongation.
Figure 4:
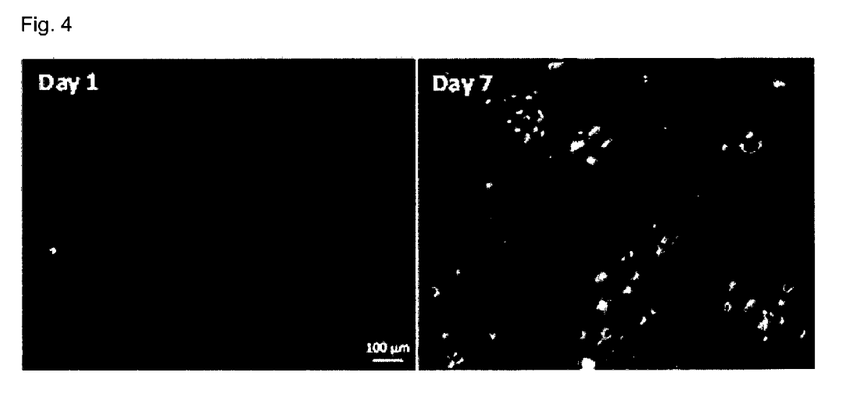
FIG. 4 Light microscopy images of primary chondrocytes in alginate sulfate gels cultured up to 7 days, so potent induction of cell proliferation, as evidence by the cell clusters present.
Figure 5:
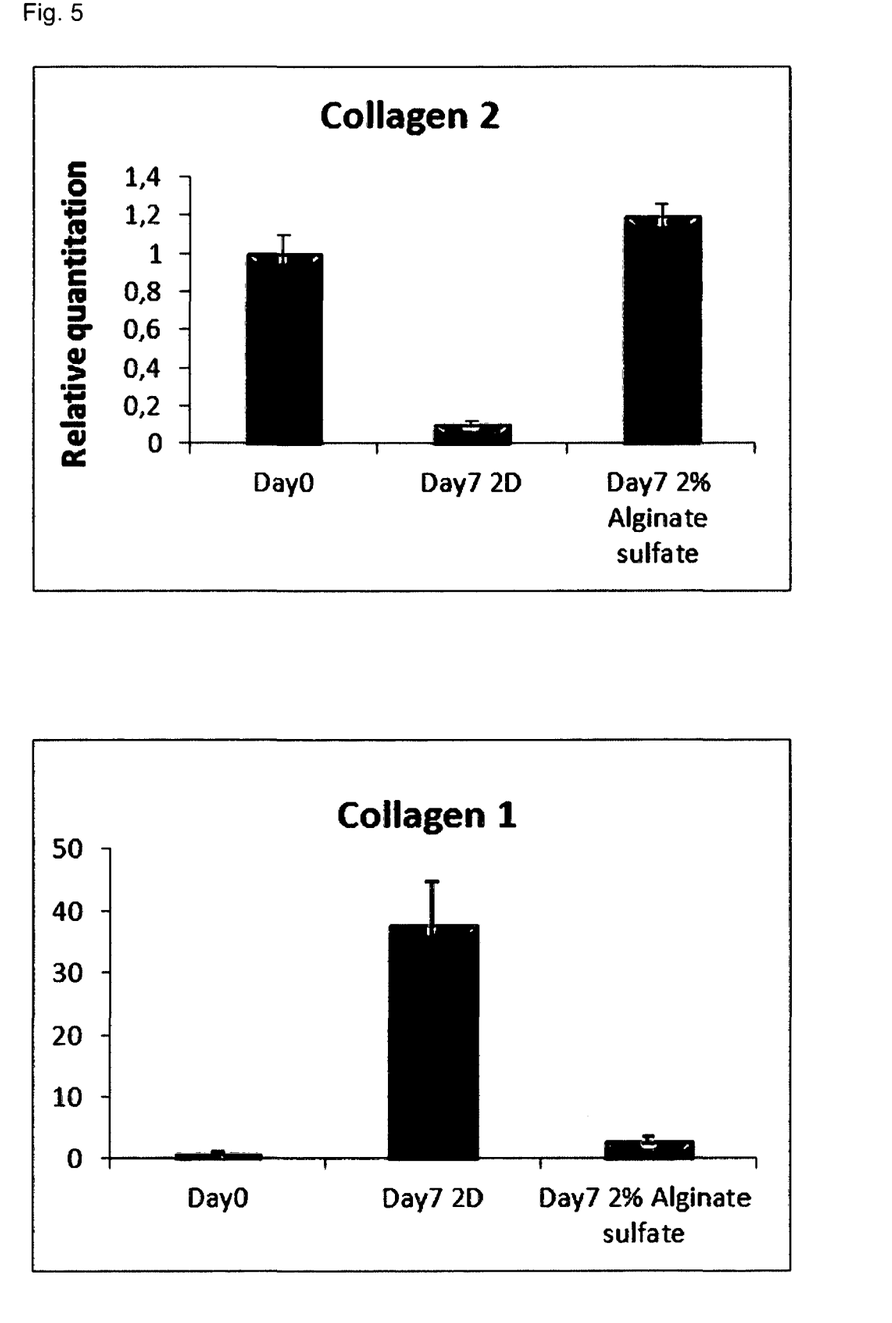
FIG. 5. Gene expression of primary chondrocytes cultured in alginate sulfate hydrogels over 7 days assessed by qRT-PCR for collagen 2 and collagen 1. Alginate sulfate can repress high collagen 1 expression which is typical of chondrocytes cultured on plastic. D0 refers to the gene expression of freshly isolated cells.

E17 rat primary cortical and hippocampal neurons were grown within alginate sulfate (0.8-1 DSs) over a period of 21 days and extended a dense neurite network already observed at day 7 (FIG. 2). The interaction between alginate sulfate and neurons could be attributed to the electrostatic bond between the sulfate and the cell membrane receptors (FIG. 3) as it is described for HSPG [Coles et al., Science. 2011; 332:484-8].

Figure 6:
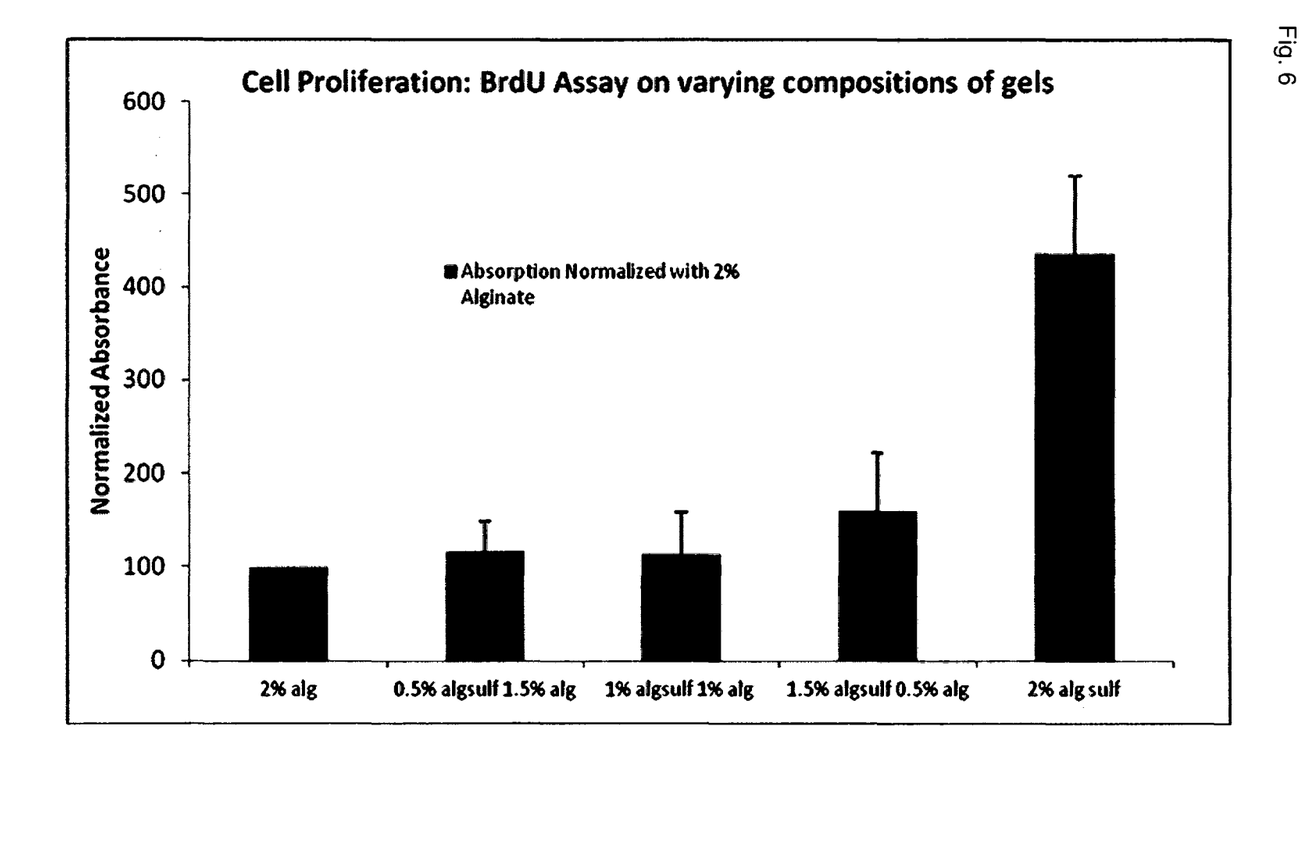
FIG. 6. BrdU cell proliferation assay of chondrocytes in sulfated alginate hydrogels. Absorbance normalized by relative quantitation of absorbance value (450 nm-540 nm blanked) to 2% alginate gels.
Figure 7:
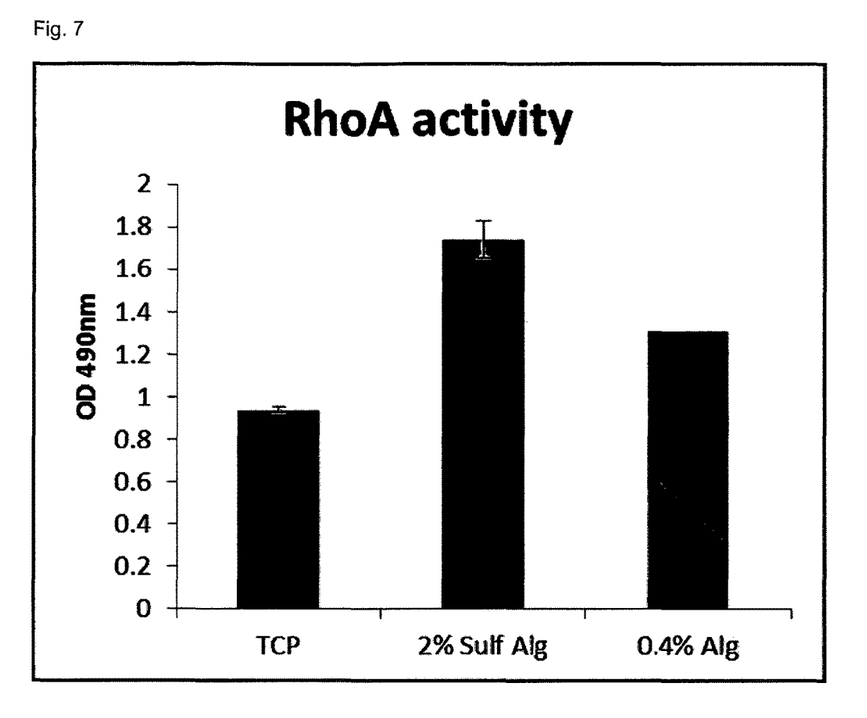
FIG. 7. RhoA activity of chondrocytes seeded within 2% alginate sulfate gels compared to tissue culture plastic (TCP) and 0.4% alginate has been evaluated by Rho G-LISA Assay (Cytoskeleton, Inc.) in 7 day cultures. RhoA activity was increased by encapsulation of the cells within alginate sulfate compared to unmodified alginate and tissue culture plastic.

For cartilage engineering applications, alginate sulfate had a potent influence on proliferation as evidenced by bromodeoxyuridine (BrdU) measurements (FIG. 6). The encapsulation of chondrocytes within alginate sulfate induced cell spreading after 3-4 days. However, the most potent effect is on proliferation, particularly there is a dose-dependent increase in proliferation with increasing amounts of sulfated alginate. The material provides a way of growing cells with in vitro or in vivo, in a way that maintains their phenotype better than 2D expansion on plastic. Furthermore, alginate sulfate induced RhoA GTPase activity (FIG. 7), which can explain the increased cell growth.

In conclusion, alginate sulfate is an abundant biomaterial, which is easily modified, processed and handled and is useful for a broad range of applications in tissue regeneration.

EXAMPLES

Example 1

Preparation of an Alginate Tetrabutyl Ammonium Salt and Alginate Sulfate 2 g alginate is dissolved in 400 ml water, and 40 g DOWEX ion exchanger that was previously charged with tetrabutyl ammonium chloride are added. The mixture is stirred over night, filtered and isolated by lyophilization.

1 g alginate tetrabutyl ammonium salt is suspended in 100 ml dry DMF. Now, a 12-fold excess $SO_3$/DMF per disaccharide repeating unit are added and the mixture is stirred at room temperature for 1 h. The opaque solution is precipitated in acetone, brought to pH 12 for 10 minutes and subsequently neutralized. The precipitate is filtered, dissolved in water and purified by dialysis. Lyophilization gives the pure product. The degree of sulfation was determined by elemental analysis to be $DS_s$=1.1 (per disaccharide unit).

Example 2

Preparation of Alginate Methacrylate 1 g alginate is dissolved in 100 ml water and a 10-fold excess glycidyl methacrylate per disaccharide repeating unit is added. The mixture is stirred for 24 h at 50° C. Now 2 ml of a 20% solution of glycine in water is added and the solution is stirred for another 30 min at 50° C. After cooling to room temperature the product is purified and isolated by dialysis and lyophilization. The degree of methacrylation $DS_{MA}$ was estimated based on the $^1$H-NMR spectra to be 0.6 (per disaccharide unit).

Example 3

Preparation of Alginate Sulfate using Chlorosulfonic Acid

Dry alginate (1 g) was added to chlorosulfonic acid and formamide for a volume of 40 ml and reacted for up to 4 hrs between 50-70° C. Alginate was precipitated through the addition of acetone and collected through centrifugation. The alginate was suspended in aqueous media, purified through dialysis and lyophilized. The degree of sulfation was estimated by elemental analysis.

Example 4

Encapsulation of Primary Neurons and iPSCs in Alginate Sulfate

Dissociated primary hippocampal or cortical neurons derived from E17-18 rat embryos or iPSCs can be encapsulated in soft hydrogels containing alginate sulfate. In particular, primary neurons are encapsulated at the density of e7 cells/ml in 2-5% alginate sulfate or in mixtures 0.1%-2% alginate:alginate sulfate (1:0-1:5). Neurospheres of iPSCs are encapsulated as 3-6 clusters/30 microliter gel. To generate 3D cultures, the gel solution is prepared in 150 mM NaCl and mixed with the cells prior to gelation. Cell-hydrogel mixtures are put into a caster (Q-gel) and this is soaked into a buffer (150 mM NaCl or culture medium) supplemented with CaCl (from 10 mM to 100 mM) for 10 min. Afterwards, gels are moved to culture plates and incubated in the same conditions for the next 10 min. Then 3D cultures are put in fresh medium without any additional calcium chloride and maintained in culture up to 21 days.

Example 5

Encapsulation of Freshly Isolated Primary Chondrocytes in Alginate Sulfate

Primary chondrocytes isolated from bovine/human knees can be encapsulated in alginate sulfate hydrogels. Alginate sulfate is dissolved in 150 mM NaCl at a concentration ranging from 2-5% w/v. Chondrocytes are resuspended in alginate sulfate with a density from 1 million to 10 million per milliliter polymer solution. For gelation, 30 microliters of cell suspension is put on a Q-gel caster and soaked in 102 mM $CaCl_2$ solution and incubated for 10 minutes. The formed gels are then freed from the caster and further incubated in 50 mM $CaCl_2$ solution. Finally, the gels are transferred to a 24-well plate with 3 mM $CaCl_2$ containing medium and cultured for up to three weeks.

The invention claimed is:

1. A cellular graft comprising a mammalian cell embedded in a hydrogel polymer composition, wherein the polymer of said composition consists of sulfated alginate having a degree of sulfation between 0.1 and 1 per monomer, and wherein the hydrogel polymer composition has a content of sulfated alginate of 0.1 to 5% (m/m).

2. The cellular graft according to claim 1, wherein the embedded mammalian cell is obtained or obtainable by a method comprising: providing a sulfated alginate in aqueous solution, wherein said sulfated alginate has a degree of sulfation between 0.1 and 1 per monomer; reacting said sulfated alginate to form a hydrogel in a gelation step, providing a precursor cell, and embedding said precursor cell in said sulfated alginate hydrogel in an embedding step.

3. The cellular graft according to claim 1, wherein said mammalian cell is a central primary neuron, a peripheral primary neuron, or a glial cell, a primary chondrocyte, or a mesenchymal stem cell, or a fibroblast, an osteoblast, a hepatocyte, an adult stem cell or an induced pluripotent cell.

4. A method for treating a cartilage lesion comprising transplanting the cellular graft of claim 1, as an augmentation of an autologous chondrocyte implantation procedure.

5. The method according to claim 4, wherein said sulfated alginate hydrogel is cross-linkable to cartilage tissue via Schiff-based covalent binding of an oxidized sulfated alginate within said sulfated alginate hydrogel.

6. The cellular graft according to claim 1, wherein said sulfated alginate hydrogel is characterized by a viscosity of 180 to 220 Pa/s.

7. The cellular graft according to claim 1, wherein said sulfated alginate is further modified by aldehyde moieties, carboxyl moieties, amino moieties, vinyl sulfone moieties, thiol moieties, saturated or unsaturated ester or ether groups.

8. The cellular graft according to claim 1, wherein said mammalian cell is a primary chondrocyte.

9. The cellular graft according to claim 6, wherein said sulfated alginate is characterized by a viscosity of about 200 Pa/s.

* * * * *